United States Patent
Cong et al.

(10) Patent No.: US 11,083,436 B2
(45) Date of Patent: Aug. 10, 2021

(54) ULTRASONIC IMAGE ANALYSIS SYSTEMS AND ANALYSIS METHODS THEREOF

(71) Applicant: SHENZHEN MINDRAY BIO-MEDICAL ELECTRONICS CO., LTD., Shenzhen (CN)

(72) Inventors: Longfei Cong, Shenzhen (CN); Yong Li, Shenzhen (CN); Long Xu, Shenzhen (CN); Lei Zhu, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 699 days.

(21) Appl. No.: 14/921,915

(22) Filed: Oct. 23, 2015

(65) Prior Publication Data
US 2016/0045186 A1 Feb. 18, 2016

Related U.S. Application Data

(63) Continuation of application No. PCT/CN2013/084044, filed on Sep. 24, 2013.

(30) Foreign Application Priority Data

Apr. 25, 2013 (CN) .......................... 201310147583.6

(51) Int. Cl.
*A61B 8/08* (2006.01)
*A61B 8/00* (2006.01)

(52) U.S. Cl.
CPC ............ *A61B 8/5207* (2013.01); *A61B 8/463* (2013.01); *A61B 8/466* (2013.01); *A61B 8/481* (2013.01);
(Continued)

(58) Field of Classification Search
None
See application file for complete search history.

(56) References Cited

U.S. PATENT DOCUMENTS

| | | | |
|---|---|---|---|
| 9,715,757 B2* | 7/2017 | Ng | ......................... G06T 15/08 |
| 2006/0020204 A1* | 1/2006 | Serra | ..................... A61B 8/0833 |
| | | | 600/437 |

(Continued)

FOREIGN PATENT DOCUMENTS

| | | |
|---|---|---|
| CN | 1961841 A | 5/2007 |
| CN | 101252886 A | 8/2008 |

(Continued)

*Primary Examiner* — Jonathan Cwern
(74) *Attorney, Agent, or Firm* — Kory D. Christensen (57) ABSTRACT

Embodiments of the present disclosure provides an ultrasonic image analysis system which includes an image collection unit which receives and transmits an ultrasonic waveform and obtains two sets of three-dimensional ultrasonic image data; an image analysis unit which registers the two sets of three-dimensional ultrasonic image data to obtain a registration mapping relationship between the two sets of three-dimensional ultrasonic image data; a user interface unit which responds to a treatment done on the two sets of three-dimensional ultrasonic image data by a user through an external hardware device; an image display unit which displays the two sets of three-dimensional ultrasonic image data according to the registration mapping relationship and a result of the treatment of the user interface unit; and an image store unit for storing the two sets of three-dimensional ultrasonic image data and the registration mapping relationship.

16 Claims, 5 Drawing Sheets

(52) U.S. Cl.
CPC ............ *A61B 8/483* (2013.01); *A61B 8/5246* (2013.01); *A61B 8/56* (2013.01)

(56) References Cited

U.S. PATENT DOCUMENTS

| | | | | |
|---|---|---|---|---|
| 2007/0010743 | A1* | 1/2007 | Arai | G06T 7/33 600/443 |
| 2009/0018445 | A1* | 1/2009 | Schers | A61B 8/0875 600/437 |
| 2009/0156933 | A1* | 6/2009 | Gerard | G06T 7/38 600/443 |
| 2011/0282202 | A1* | 11/2011 | Lee | A61B 5/1075 600/443 |
| 2014/0125779 | A1* | 5/2014 | Ericson | H04N 13/351 348/51 |

FOREIGN PATENT DOCUMENTS

| | | | |
|---|---|---|---|
| CN | 101568942 A | 10/2009 | |
| CN | 101681504 A | 3/2010 | |

* cited by examiner

ULTRASONIC IMAGE ANALYSIS SYSTEMS AND ANALYSIS METHODS THEREOF

TECHNICAL FIELD

This disclosure relates to ultrasonic image analysis, and more particularly to a medical ultrasonic image analysis system and method.

BACKGROUND

The International Agency for Research on Cancer (IARC) affiliated with The United Nations World Health Organization (WHO) reported that in 2008, about 12.7 million people were diagnosed with cancer and approximately 7.6 million people died from cancer. In 2030, about 21.4 million people will be diagnosed with cancer and approximately 13.2 million people will die from cancer. Ultrasound interventional therapy is one the fastest growing therapies that have a clear effect on liver cancer, lung cancer and thyroid cancer. In China, liver cancer is one of the most common malignancies. Three hundred thousand people die from liver cancer each year. Among the many therapies for liver cancer, surgical removal is one of the most common. However, 80% of liver cancer patients may not be suitable for surgical removal due to poor liver function and clotting mechanism caused by liver cirrhosis, due to the location of the tumor, and/or poor heart and kidney function. For the remaining 20% of liver cancer patients, the recurrence rate of liver cancer may be up to 70% even if surgical removed. However, liver cancer cells usually may be not sensitive to radiotherapy and chemotherapy. Therefore, various non-surgical interventional treatments are used for liver cancer.

During tumor ablation treatment guided by ultrasound, ultrasound contrast imaging may be used to evaluate the effect of the interventional therapy. At present, a main evaluation method is to measure the long diameter of the tumor in two-dimensional ultrasound contrast images obtained before and after the interventional therapy. However, this method cannot ensure consistency of slices and positions between two measurements. Especially when ablation using multiple needles for large tumor is performed, a simple long diameter measurement cannot stand for a whole ablation area. Currently, three-dimensional ultrasound contrast enhancement techniques may be used to display the individual status of each target region separately or combine with 4D imaging to display dynamic blood perfusion modality of the target region. Other methods of evaluating the interventional effect may be based on tomography by a CT/MRI device. However, these methods cannot provide for real-time evaluation of a clinical operation treatment and also may lack a three-dimensional volumetric dosing comparison function for the tumor before and after tumor interventional therapy. Furthermore, usually three-dimensional contrast images of some phase may be observed individually in a clinic, but the precision rate is low.

SUMMARY

This disclosure provides ultrasonic image analysis systems and methods thereof that may evaluate the therapeutic effect on a patient directly and explicitly.

Embodiments of the present disclosure provide an ultrasonic image analysis system. The system may comprise:

an image collection unit for transmitting an ultrasonic wave and receiving an ultrasonic echo, obtaining a first set of three-dimensional ultrasonic image data based on the ultrasonic echo, transmitting an ultrasonic wave and receiving an ultrasonic echo after obtaining the first set of three-dimensional ultrasonic image data, and obtaining a second set of three-dimensional ultrasonic image data based on the ultrasonic echo; and an image analysis unit for analyzing and registering the first set of three-dimensional ultrasonic image data and the second set of three-dimensional ultrasonic image data to obtain a registration mapping relationship between the first set of three-dimensional ultrasonic image data and the second set of three-dimensional ultrasonic image data; and an image display unit for displaying the first set of three-dimensional ultrasonic image data and the second set of three-dimensional ultrasonic image data based on the registration mapping relationship.

In some embodiments, the ultrasonic image analysis system also comprises an image storage unit for storing the first set of three-dimensional ultrasonic image data, the second set of three-dimensional ultrasonic image data and/or the registration mapping relationship.

In some embodiments, the first set of three-dimensional ultrasonic image data and the second set of three-dimensional ultrasonic image data collected by the image collection unit may be three-dimensional ultrasonic tissue image data and/or three-dimensional contrast enhanced ultrasonic image data.

In some embodiments, the image analysis unit may comprise an automatic analysis sub-unit for automatically analyzing and registering the second set of three-dimensional image data and the first set of three-dimensional image data to obtain the registration mapping relationship.

In some embodiments, the image analysis unit may comprise a semi-automatic analysis sub-unit for semi-automatically analyzing and registering the second set of three-dimensional image data and the first set of three-dimensional image data in connection with a user interface unit and the image display unit to obtain the registration mapping relationship.

In some embodiments, the image display unit may also comprise:

an image reconstruction sub-unit for receiving a selection signal for selecting a target region, using one of the first set of three-dimensional ultrasonic image data and the second set of three-dimensional ultrasonic image data to reconstruct a first image of the target region, and using the other of the first set of three-dimensional ultrasonic image data and the second set of three-dimensional ultrasonic image data to reconstruct a second image of the target region corresponding to the first image based on the mapping registration relationship; and the image display unit may display the first image on a first region of a display, and may display the second image on a second region of the display.

In some embodiments, the first image or the second image may be a three-dimensional image of the target region and/or at least one section image of the target region Embodiments of the present invention may include an ultrasonic image analysis method. The method may comprise:

collecting a first set of three-dimensional ultrasonic image data;

collecting a second set of three-dimensional image data after collecting the first set of three-dimensional ultrasonic image data;

analyzing and registering the second set of three-dimensional ultrasonic image data and the first set of three-dimensional ultrasonic image data to obtain a registration mapping relationship between the first set of three-dimensional ultrasonic image data and the second set of three-dimensional image data; and displaying the first set of three-dimensional ultrasonic image data and the second set of three-dimensional ultrasonic image data based on the registration mapping relationship.

In some embodiments, the ultrasonic image analysis method may further comprise: storing the first set of three-dimensional ultrasonic image data, the second set of three-dimensional ultrasonic image data and/or the registration mapping relationship.

In some embodiments, the first set of three-dimensional ultrasonic image data and the second set of three-dimensional image data may be three-dimensional ultrasound tissue image data and/or three-dimensional contrast enhanced ultrasonic image data.

In some embodiments, analyzing and registering the first set of three-dimensional ultrasonic image data and the second set of three-dimensional ultrasonic image data may comprise automatically analyzing and registering the first set of three-dimensional ultrasonic image data and the second set of three-dimensional ultrasonic image data to obtain the registration mapping relationship.

In some embodiments, analyzing and registering the first set of three-dimensional ultrasonic image data and the second set of three-dimensional ultrasonic image data may comprise semi-automatically analyzing and registering the first set of three-dimensional ultrasonic image data and the second set of three-dimensional ultrasonic image data to obtain the registration mapping relationship.

In some embodiments, displaying the first set of three-dimensional ultrasonic image data and the second set of three-dimensional ultrasonic image data may comprise:

receiving a selection signal for selecting a target region;

using one of the first set of three-dimensional ultrasonic image data and the second set of three-dimensional ultrasonic image data to reconstruct a first image of the target region;

displaying the first image on a first region of a display;

using the other of the first set of three-dimensional image data and the second set of three-dimensional image data to reconstruct a second image of the target region corresponding to the first image based on the registration mapping relationship; and displaying the second image on a second region of the display.

In some embodiments, the first image and the second image may be a three-dimensional image of the target region and/or at least one section image of the target region.

Embodiment of the present disclosure may also include an ultrasonic image analysis method. The method may comprise:

collecting a first set of three-dimensional ultrasonic image data;

displaying the first set of three-dimensional ultrasonic image data and collecting a second set of three-dimensional ultrasonic image data under the guidance of the first set of three-dimensional ultrasonic image data;

analyzing and registering the first set of three-dimensional ultrasonic image data and the second set of three-dimensional ultrasonic image data to obtain a registration mapping relationship between the first set of three-dimensional ultrasonic image data and the second set of three-dimensional ultrasonic image data; and displaying the first set of three-dimensional ultrasonic image data and the second set of three-dimensional ultrasonic image data based on the registration mapping relationship.

In some embodiments, displaying the first set of three-dimensional ultrasonic image data and collecting the second set of three-dimensional ultrasonic image data under the guidance of the first set of three-dimensional ultrasonic image data may comprise:

displaying at least one section image of the first set of three-dimensional ultrasonic image data; and transmitting a ultrasound wave and receiving a ultrasound echo through an ultrasonic probe to obtain a section image, changing a location of the ultrasonic probe, and when the obtained section image may be similar to the at least one section image, collecting the second set of three-dimensional ultrasonic image data.

In some embodiments, displaying the first set of three-dimensional ultrasonic image data and the second set of three-dimensional ultrasonic image data based on the registration mapping relationship may comprise:

receiving a selection signal for selecting a target region;

using one of the first set of three-dimensional ultrasonic image data and the second set of three-dimensional ultrasonic image data to reconstruct a first image of the target region;

displaying the first image on a first region of a display;

using the other of the first set of three-dimensional image data and the second set of three-dimensional image data to reconstruct a second image of the target region corresponding to the first image based on the registration mapping relationship; and displaying the second image on a second region of the display.

In some embodiments, the first image or the second image may be a three-dimensional image and/or at least one section image of the target region.

Embodiments of the present disclosure include an ultrasonic image analysis system and an analysis method thereof. At least twice imaging a target region may be carried out by using three-dimensional ultrasound contrast imaging technology. Two sets of data of the target region may be collected at different times. A one-to-one mapping relationship of the two sets of data may be made based on image registration technology. The status of the target regions in different times may be displayed based on registration results. Meanwhile, based on mapping relationships between the two sets of data built by registration, operations such as measuring, tracing, dividing, etc performed on one set of data may be mapped to corresponding position of the other set of data to be displayed, thus the two set of data may be compared intuitively and the therapeutic effect can be evaluated.

DETAILED DESCRIPTION

Technical solutions will be described more clearly and completely below in connection with the embodiments of the present disclosure. It should be noted that similar or identical components may be identified with same reference numbers in the appended drawings and specification.

In clinical therapies, ultrasound may be used for interventional treatments and observations. Thermal ablation is one of the most widely carried out tumor interventional therapy technologies. However, there is no effective method for evaluating the effect of the ablation therapy in real time.

Embodiments of the present disclosure provide an ultrasonic image analysis system method. The target region may be imaged at least twice by using three-dimensional ultrasound contrast imaging technology to obtain two sets of data of the target region at different times. A one-to-one mapping relationship of the two sets of data may be built based on the image registration technology and status of the target region at different times may be displayed based on registration results. Meanwhile, based on the mapping relationships between the two sets of data built by registration, operations such as measuring, tracing, dividing, etc., performed on one set of data may be mapped to a corresponding position of the other set of data to be displayed. Thus the two set of data may be compared intuitively and the therapeutic effect can be evaluated.

Figure 1:
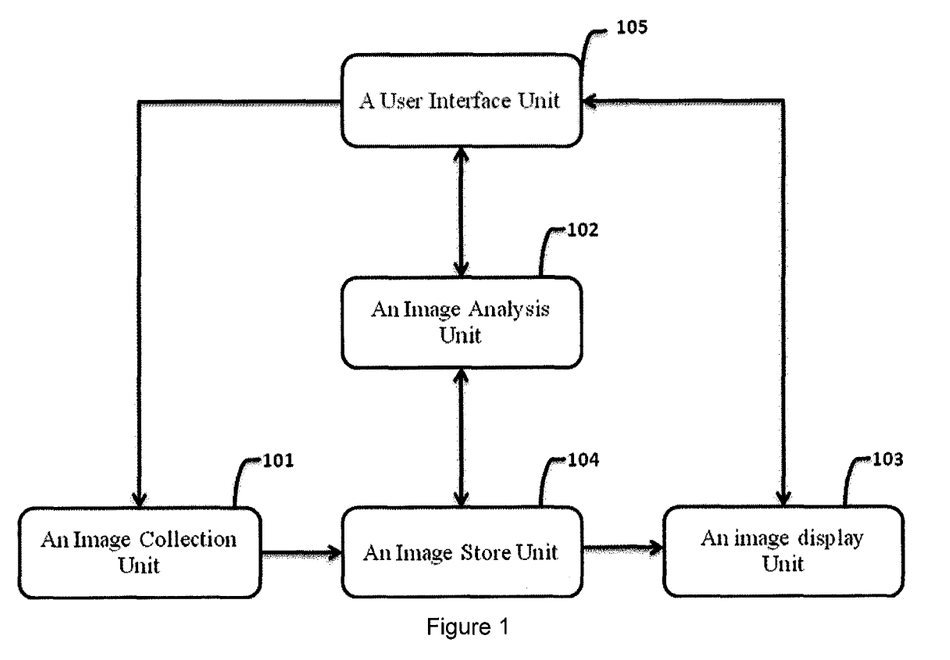
FIG. 1 is schematic diagram of an ultrasonic image analysis system according to the present disclosure.

As illustrated in FIG. 1, in some embodiments, the ultrasonic image analysis system may include an image collection unit 101. The image collection unit 101 may transmit ultrasonic waves and receive ultrasonic echoes through an ultrasonic probe and process the ultrasonic echoes to obtain three-dimensional ultrasonic image data. In some embodiments, the three-dimensional ultrasonic image data collected by the image collection unit 101 may be three-dimensional ultrasonic tissue image data and/or three-dimensional contrast enhanced ultrasonic image data.

During the collection of the three-dimensional ultrasonic image data, at least two set of three-dimensional ultrasonic image data (i.e. the first set of three-dimensional ultrasonic image data and the second set of three-dimensional ultrasonic image data) of scanned object may be collected by the image collection module or unit 101, which may be implemented, as with the other described modules or units, using hardware, software, or a combination thereof.

In the process of collection, various collection angles and collection scope may used to obtain the richest data information for the following registering operation. A time interval between the two sets of three-dimensional ultrasonic image data may be established, and operations such as other scans or tumor ablation operations can be performed in the time interval. During the two collections, the positions of the patient can be kept consistent, and the directions and positions of the ultrasonic probe can be kept consistent.

The specific contrast imaging and three-dimensional ultrasonic contrast imaging processes may use known technologies in the art, which will not be described in detail here.

The ultrasonic image analysis system may further include an image analysis unit 102. The image analysis unit 102 may analyze and register the first set of three-dimensional ultrasonic image data and the second set of three-dimensional ultrasonic image data to obtain a registration mapping relationship between the first set of three-dimensional ultrasonic image data and the second set of three-dimensional ultrasonic image data. The analysis and registering may be based on the three-dimensional ultrasonic tissue image data, the three-dimensional contrast enhanced ultrasonic image data, or based on a combination thereof.

In some embodiments, the image analysis unit 102 may comprise an automatic analysis sub-unit. The automatic analysis sub-unit may automatically analyze and register the second set of three-dimensional image data and the first set of three-dimensional image data to obtain the registration mapping relationship.

In some embodiments, the image analysis unit 102 may comprise a semi-automatic analysis sub-unit, which may semi-automatically analyze and register the second set of three-dimensional image data and the first set of three-dimensional image data in connection with a user interface unit and the image display unit to obtain the registration mapping relationship.

The ultrasonic image analysis system may further include a user interface unit 105. The user interface unit 105 may respond to inputs input by the user through external hardware devices to the first set of three-dimensional ultrasonic image data and the second set of three-dimensional ultrasonic image data.

The ultrasonic image analysis system may further include an image display unit 103. The image display unit 103 may display the first set of three-dimensional ultrasonic image data, the second set of three-dimensional ultrasonic image data and the disposal result of the user interface unit 105 based on the registration mapping relationship.

In some embodiments, the ultrasonic image analysis system may further include an image storage unit 104. The image storage unit 104 may store the first set of three-dimensional ultrasonic image data, the second set of three-dimensional ultrasonic image data and/or the registration mapping relationship.

In some embodiments, the image display unit 103 may include an image reconstruction sub-unit. The image reconstruction sub-unit may receive a selection signal for selecting a target region, use one of the first set of three-dimensional ultrasonic image data and the second set of three-dimensional ultrasonic image data to reconstruct a first image of the target region, and use the other of the first set of three-dimensional ultrasonic image data and the second set of three-dimensional ultrasonic image data to reconstruct a second image of the target region corresponding to the first image based on the mapping registration relationship.

The image display unit 103 may display the first image on a first region of a display, and display the second image on a second region of the display.

In some embodiments, the image display unit 103 may further include an image measuring sub-unit. The measuring sub-unit may measure and edit the first set of three-dimensional ultrasonic image data, the second set of three-dimensional ultrasonic image data and the registration mapping relationship generated by the image analysis unit 102.

Automatic registration methods mainly include two categories: methods based on similarity measurement between images and methods based on mapping between images. For methods based on different mapping methods, they may be classified into rigid transformation (rotation and translation, i.e. rigid registration) methods, radioactive transformation (scaling, rotation and translation, i.e. radioactive registration) methods and nonlinear transformation (building different mapping for different parts of images, i.e. nonlinear registration) methods. In connection with ultrasonic three-dimensional contrast imaging, two embodiments involving rigid registration and radioactive registration may be provided. However, the embodiments may be not limited to a specific registration method. If two sets of contrast data may be collected in the same depth, i.e. the collected pixels may be in the same scale, registration method may be limited to rigid registration, such as rotation and translation. If depths of two collections may be different, i.e. the collected image pixels may be not in the same scale, two sets of data may be scaled into the same scale by using bilinear interpolation, and then be registered according to rigid registration.

Assuming an intensity of a pixel $X_i$ in one set of three-dimensional ultrasonic contrast data as $f(X_i)$ and an intensity of a pixel $Y_i$ in the other set of three-dimensional ultrasonic contrast data as $g(Y_i)$, a mapping between the two sets of three-dimensional contrast image data may be expressed as:

$$X_i = AY_i, X_i = \begin{bmatrix} x_1^i \\ x_2^i \\ x_3^i \\ 1 \end{bmatrix}, Y_i = \begin{bmatrix} y_1^i \\ y_2^i \\ y_3^i \\ 1 \end{bmatrix}, A = \begin{bmatrix} a_{11}, a_{12}, a_{13}, T_1 \\ a_{12}, a_{22}, a_{23}, T_2 \\ a_{31}, a_{32}, a_{33}, T_3 \\ 0, 0, 0, 1 \end{bmatrix} \quad (1)$$

Meanwhile, a similarity measurement function of the two sets of image data may be defined as:

$$E = \sum_{i=1...N} |f(X_i) - g(AX_i)|$$

The similarity measurement described above may be a typical "minimum sum of absolute difference." An analogous definition may be "minimum sum of square difference," "maximum cross correlation," and minimum absolute difference improved based on Rayleigh distributional characteristics of noise of an ultrasonic wave. Meanwhile, the $f(X_i)$ and $g(Y_i)$ in the similarity measurement function may also be defined as size of local gradient or gray entropy of corresponding data, etc.

When performing image registration, instead of the automatic registration method described above, a semi-automatic registration method, i.e. an interactive registration method associated with the user interface unit 105 and the image display unit 103, may be used. Under an assumption of rigid registration, a matrix of 3×3 in an upper-lift corner of a mapping matrix A may be a symmetric orthogonal matrix. There may be many rigid registration methods for solving the rigid registration between two sets of three-dimensional ultrasonic image data, and the most direct method may be using interactive operation, i.e. selecting 4 sets or more than 4 sets of pairs of corresponding points in the two sets of three-dimensional ultrasonic data and solving the most optimum mapping matrix A by using least square fit method. It may be also possible to select one section in each of the two sets of three-dimensional ultrasonic image data, build a one-to-one relationship between the two sections by using fusion display method, and select a pair of corresponding points which may be outside of the two sections. In some embodiments, a combination of the interactive registration method and the automatic registration method may be used to perform the image registration.

Figure 2:
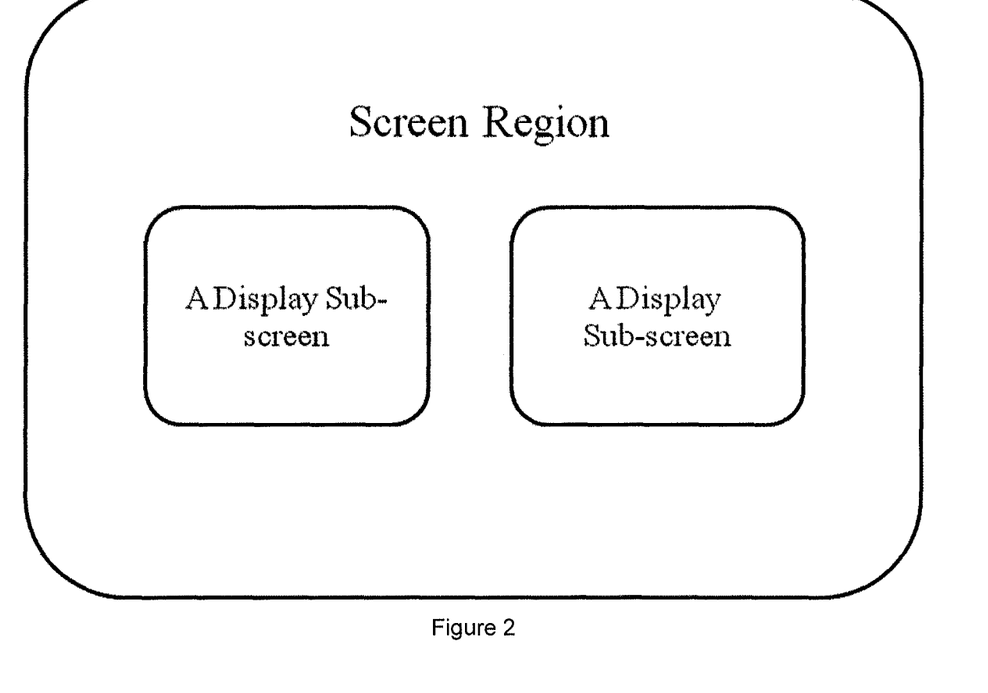
FIG. 2 is an exemplary user interface displayed by an image display unit of an embodiment of an ultrasonic image analysis system according to the present disclosure.

After the registration operation, the registration result may be displayed based on the image display unit 103. As illustrated in FIG. 2, the screen region of the image display unit 103 may at least include two sub-screens to comparatively display the two sets of data. The displayed registration results may be the three-dimensional ultrasound tissue image data, the three-dimensional contrast enhanced ultrasound image data or a combination thereof.

The image display unit 103 may include image multiplanar reconstruction functions, which, in connection with the user interface unit 105, may select a target region in the images and perform multiplanar reconstruction for the target region. The sections reconstructed may be the three-dimensional ultrasonic tissue image, and may also be three-dimensional contrast enhanced ultrasonic image. The reconstructed two sets of images may be displayed respectively on the sub-screens. For example, the images reconstructed from the first set of three-dimensional contrast enhanced ultrasonic image data may be displayed on one of the sub-screens, and the images reconstructed from the second set of three-dimensional contrast enhanced ultrasonic image data, which correspond to the images reconstructed from the first set of three-dimensional contrast enhanced ultrasonic image data, may be displayed on the other of the sub-screens. Image pixels displayed on the two sub-screens may have a one-to-one correspondence. The images displayed on the two sub-screens may be three-dimensional contrast enhanced ultrasonic image data, and may also be three-dimensional ultrasonic tissue image data, and also may be switched between these two kinds of data.

The first set of three-dimensional ultrasonic image data and the second set of three-dimensional image data displayed by the image display unit 103 may include, but not limit to, a part, one section, or multiple sections of the first set of three-dimensional ultrasonic image data and the second set of three-dimensional ultrasonic image data, and projections of the first set of three-dimensional ultrasonic image data or the second set of three-dimensional ultrasonic image data in a certain direction.

In some embodiments, measurement function may also be supported by the two sub-screens, such as distance measurement, area measurement, crispening or tracing etc. Linkage display may be also supported by the two displaying sub-screen, i.e. a measuring operation being performed on one sub-screen may be simultaneously displayed on the other sub-screen at the same position. The linkage display may also be disabled and the measuring operation may be performed on one sub-screen separately. In some embodiments, one section may be displayed on the sub-screen described above. In some embodiments, multiple sections may be displayed on the sub-screen, i.e., images arrayed in the same sequence may be displayed on the two sub-screens. The user may select different section (for example, reconstructed) on the screen of the image displaying unit 103 to be displayed and measured.

In some embodiments, several ultrasonic image analysis methods may be provided, which will be described in details below.

Figure 3:
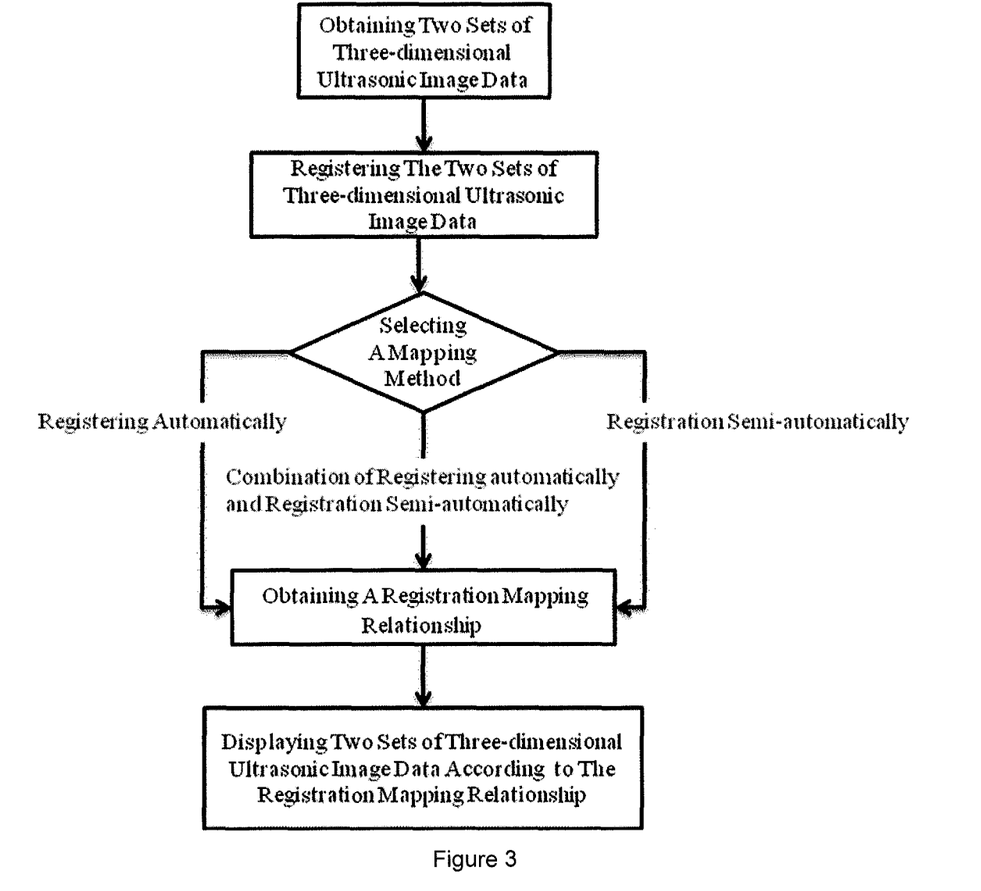
FIG. 3 is a first flow diagram of an ultrasonic image analysis method according to the present disclosure.

As illustrated in FIG. 3, an ultrasonic image analysis method may proceed as follows.

A first set of three-dimensional ultrasonic image data and the second set of three-dimensional ultrasonic image data may be collected in the image collection unit 101. Specific collecting methods may be similar to a process of collecting three-dimensional ultrasonic image data described above, which will not describe in detail.

The first set of three-dimensional ultrasonic image data and the second set of three-dimensional ultrasonic image data may be registered to obtain a relationship between the first set of three-dimensional ultrasonic image data and the second set of three-dimensional ultrasonic image data. Specific registration methods of three-dimensional ultrasonic image data may include automatic registering methods or semi-automatic registering methods, and also may be a combination of the two methods to analyze and register the two sets of three dimensional ultrasonic image data.

The first set of three-dimensional ultrasonic image data and the second set of three-dimensional ultrasonic image data may be displayed in the image display module 103 based on the registration mapping relationship.

In some embodiments, the first set of three-dimensional ultrasonic image data and the second set of three-dimensional ultrasonic image data may be displayed based on the registration mapping relationship, which may include steps described below.

First, selected signals of a selected target region are received. The selected signals may be input by user though a user interface unit 105, and also may be a system default. A target region of interest to a user may be confirmed through the selected signals. The target region may be a part of the first set of three-dimensional ultrasonic image data or the second set of three-dimensional image data. In other words, the target region may be selected from the first set of three-dimensional image data or the second set of three-dimensional image data.

One of the first set of three-dimensional ultrasonic image data and the second set of three-dimensional ultrasonic image data may be used to reconstruct a first image of the target region to display the first image on the first region of a display.

The other set of three-dimensional ultrasonic image data from the first set of three-dimensional ultrasonic image data and the second set of three-dimensional ultrasonic image data may be used to reconstruct a second image in a target region corresponding to the first image based on the registration mapping relationship. It will be understood that that because the registration mapping relationship between two sets of three-dimensional ultrasonic image data have been obtained already, a region corresponding to the target region from the other three-dimensional ultrasonic image data may be obtained and an image of the corresponding region using the other three-dimensional ultrasonic image data may be reconstructed, i.e. the second image of the target region corresponding to the first image as mentioned, and the second image may be displayed on the second region of a display.

In some embodiments, the first image and the second image may be a three-dimensional image and/or at least a section image of the target region.

Figure 4:
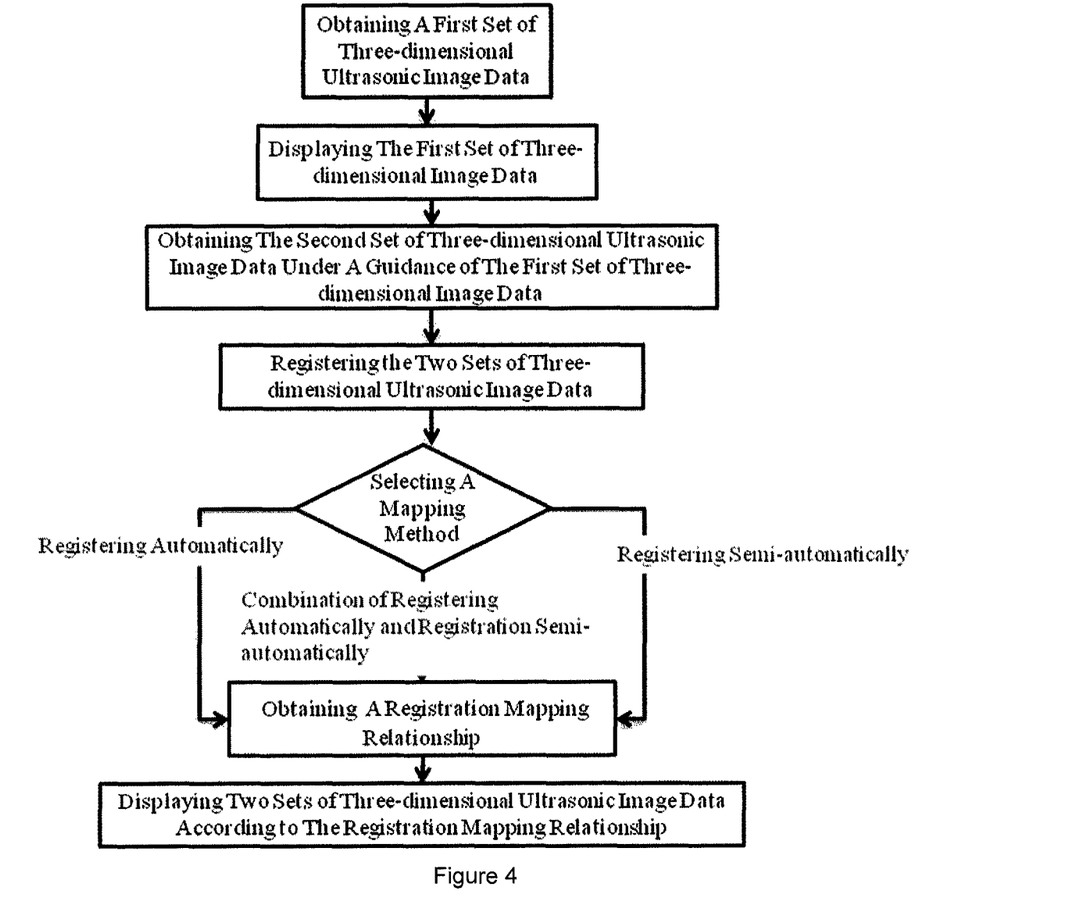
FIG. 4 is a second brief flow diagram of an ultrasonic image analysis method according to the present disclosure.

As illustrated in FIG. 4, an ultrasonic image analysis method may proceed as described below.

A first set of three-dimensional ultrasonic image data may be collected.

The first set of three-dimensional ultrasonic image data and collecting the second set of three-dimensional ultrasonic image data may be displayed under a guidance of the first set of three-dimensional ultrasonic image data.

The first set of three-dimensional ultrasonic image data and the second set of three-dimensional ultrasonic image data may be registered to obtain a registration mapping relationship between the first set of three-dimensional ultrasonic image data and the second set of three-dimensional ultrasonic image data.

The first set of three-dimensional ultrasonic image data and the second set of three-dimensional ultrasonic image data may be displayed based on the registration mapping relationship.

In some embodiments of the present disclosure, the first set of three-dimensional ultrasonic image data may be displayed and the second set of three-dimensional ultrasonic image data may be collected under a guidance of the first set of three-dimensional ultrasonic image data, as described below.

At least one section image of the first set of three-dimensional ultrasonic image data may be displayed. An ultrasound wave may be transmitted and an ultrasound echo received through an ultrasonic probe to obtain section images. A location of the ultrasonic probe may be changed. When section image obtained may be similar to the at least one section image, the method may proceed by beginning to collect the second set of three-dimensional ultrasonic image data.

For example, when the first set of three-dimensional ultrasonic image data may be collected, target regions to be evaluated may be involved. The first set of three-dimensional ultrasonic image data collected may be sent to the image display unit 103 and may be displayed in some displaying sub-unit in a region of the display of the image display unit 103. Then the second set of three-dimensional image data may be collected. For example, some section of the first set of three-dimensional ultrasonic image data (i.e. a section in some certain direction may include, but not limited to, an axial section in the middle of the three-dimensional ultrasonic image data) may be displayed in a display sub-screen. The same section may be found by moving an ultrasonic probe before collecting three-dimensional ultrasonic image data the second time, and the second set of the three-dimensional ultrasonic image data may be collected. Positions of the ultrasonic probes and directions of the ultrasonic probes of two data collections may be assured to be consistent, so to ensure that the collecting data represent the same part of a body. Two sets of three-dimensional data may be registered by using image analysis registration method of the image analysis unit 102. Specifically, registration may be automatically performed based on an image processing algorithm, and also may be semi-automatically performed in connection with manual interactive operation (i.e. interactive registration).

In some embodiments, a method of displaying the first set of three-dimensional ultrasonic image data and the second set of three-dimensional ultrasonic image data based on the registration mapping relationship may be the same as the second method mentioned above.

Figure 5:
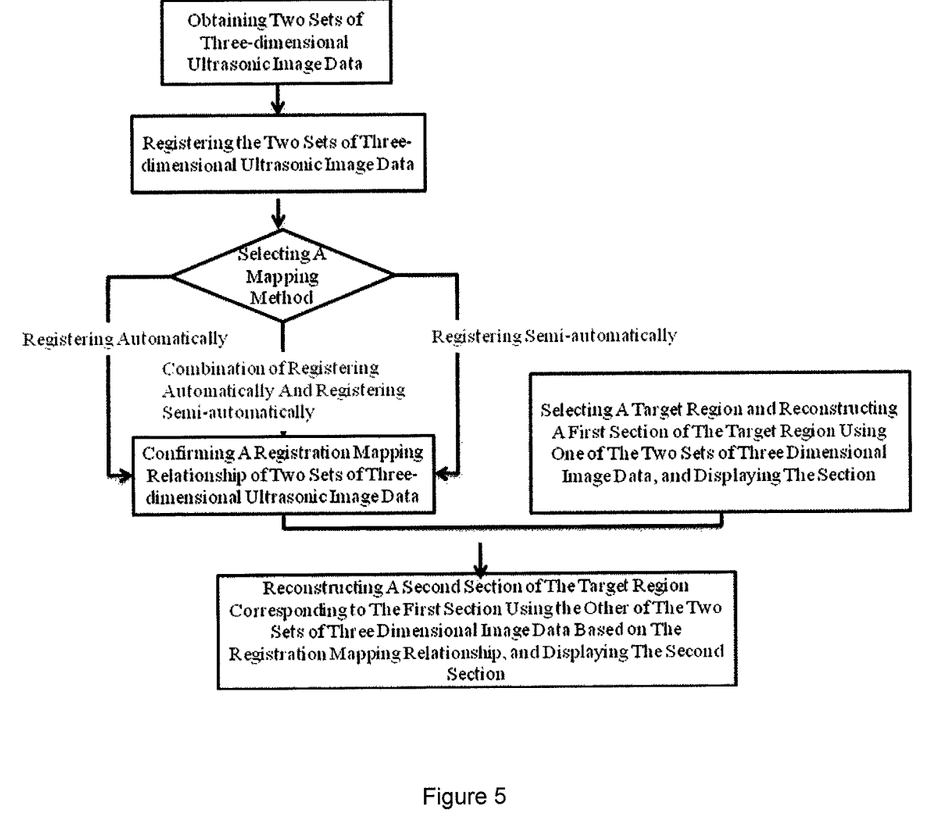
FIG. 5 is a third flow diagram of an ultrasonic image analysis method according to the present disclosure.

As illustrated in FIG. 5, an ultrasonic image analysis method may include followings steps.

Two sets of three-dimensional ultrasonic image data may be collected by the image collection unit 101 as described above. Specific collection methods may be similar to those described above, which will not be described in detail.

The two sets of three-dimensional image data collected may be registered and the registration mapping relationship may be confirmed between the two sets of three-dimensional ultrasonic image data. Specific registration methods of three-dimensional ultrasonic image data may use an automatic registration mapping method or a semi-automatic registration mapping method as described above, and also may be a combination of the two methods thereof to register the two sets of three-dimensional ultrasonic image data, which will not be described in detail.

A target region among a set of three-dimensional ultrasonic image data thereof may be selected, a section of the target region may be reconstructed according to a selected direction, and displaying the direction of the set of three-dimensional ultrasonic image data. Based on the registration mapping relationship of the two sets of image, a section corresponding to the section reconstructed before may be reconstructed among the other set of three-dimensional ultrasonic image data and may be displayed.

The image may be used to reconstruct a sub-unit, the image data collected may be reconstructed in two collections in the target region, the target region in three-dimensional image data may be selected and multiplanar of the target may be reconstructed. The image data reconstructed may have a one-to-one correspondence. A reconstructed section may be three-dimensional ultrasonic tissue image data or three-dimensional ultrasonic contrast image data. For example, images reconstructed from the first set of three-dimensional ultrasonic image data may be displayed in one of the displaying sub-screens. Images reconstructed from the second set of three-dimensional ultrasonic image data corresponding to the former images may be displayed in the other sub-screen. Image pixels displayed in the two sub-screens may have a one-to-one correspondence.

The three-dimensional ultrasonic image data may be stored and the registration result. The three-dimensional ultrasonic image data and the registration result may be stored in the image storage module 104.

In some embodiments, as any ultrasonic image analysis method described above, the three-dimensional ultrasonic image data may be three-dimensional ultrasonic tissue image data or three-dimensional contrast image data, and also may be a combination of the same.

In some embodiments, as any ultrasonic image analysis methods described above, the image registration may include the following: the three-dimensional ultrasonic image data may be registered automatically and registration results may be generated. Specific automatic analysis and registration methods may be consistent with the automatic registration methods described above, which will not be described in detail.

In some embodiments, as any ultrasonic image analysis method described above, the images registration includes the following: the three-dimensional ultrasonic image data may be registered semi-automatically and registration results may be generated. Specific automatic registration methods may be consistent with the semi-automatic registration methods described above, which will not be described in detail.

In some embodiments, as any ultrasonic image analysis method described above, the multiplanar reconstructions of the three-dimensional ultrasonic image data and registration results may be performed. Specific function of multiplanar reconstructions may be consistent with the multiplanar reconstructions described above, which will not be described in detail.

In some embodiments, as any ultrasonic image analysis methods described above, the three-dimensional ultrasonic image data and the registration results may be measured and edit. Specific effects of measurement and edit may be consistent with the measurement and edit described above, which will not be described in detail.

In embodiments of the present disclosure, clinical tumor interventional therapies may be imaged for pre-operation and post-operation at least twice by using three-dimensional ultrasound contrast imaging devices. Two sets of data of a target region may be obtained in different time. The two set of data may be registered by using image processing techniques. A one-to-one mapping relationship between the two sets of data may be built by using image processing techniques to register the two sets of data. The status of target regions at different times based on the registration results may be displayed based on a registration result comparison. Meanwhile, the corresponding locations of the other set of data may be mapped to display based on the mapping relationship between two sets of data constructed by registration, thus the two set of data may be compared directly. Whether an ablation effect region covers a whole tumor region may be evaluated by calculating, tracing, dividing, etc. Thus, the two set of data may be compared directly. The ablation effect may be evaluated on site. If ablation may not cover the whole tumor region, complementary needle ablation may be done on site. Delayed time of clinical evaluation and secondary interventional operation may be avoided based on CT/MRI etc.

The embodiments described above may be merely used to illustrate the technical solutions of the present disclosure, but should not be deemed as limitations to the scope of this disclosure. It should be noted that, for those of ordinary skill in the art, without departing from the inventive concept of this disclosure, a number of variations and modifications may be made, while such variations or modifications should be deemed to be included within the scope of this disclosure. Accordingly, the scope of protection of this disclosure should be defined by the appended claims.

The invention claimed is:

1. An ultrasonic image analysis system, comprising:
    an image collection unit comprising an ultrasonic probe and a processor, wherein the image collection unit:
        transmits ultrasonic waves to a target region and obtains a first set of three-dimensional ultrasonic image data corresponding to the target region before ablation;
        displays a pre-ablation section image from the first set of three-dimensional ultrasonic image data;
        transmits ultrasonic waves to the target region and obtains real time post-ablation section images of the target region as a user changes a location of the ultrasonic probe; and
        when one of the post-ablation section images is determined to be similar to the pre-ablation section image, transmits ultrasonic waves to the target region at the location of the ultrasonic probe and obtains a second set of three-dimensional ultrasonic image data corresponding to the target region after ablation;
    an image analysis unit comprising the processor which registers the first set of three-dimensional ultrasonic image data and the second set of three-dimensional ultrasonic image data to obtain a one-to-one registration mapping relationship between the first set of three-dimensional ultrasonic image data and the second set of three-dimensional ultrasonic image data, wherein the one-to-one registration mapping relationship is obtained from only either or both of the first set of three-dimensional ultrasonic image data and the second set of three-dimensional ultrasonic image data, the image analysis unit being coupled to the image collection unit; and
    an image display unit, which comparatively displays a first image generated from the first set of three-dimensional ultrasonic image data in a first display area and a second image generated from the second set of three-dimensional ultrasonic image data based on the one-to-one registration mapping relationship in a second display area next to the first display area, the image display unit being coupled to the image analysis unit;
    wherein the first and second display areas are linked, such that a measuring operation performed on the first image is simultaneously displayed at a same position on the second image, and measuring operation performed on the second image is simultaneously displayed at a same position on the first image, in order to evaluate a therapeutic effect of the ablation, wherein the measuring operation comprises at least one of a distance measuring operation, an area measurement operation, or a tracing of the target region.

2. The ultrasonic image analysis system of claim 1, further comprising:
an image storage device comprising a memory component which stores the first set of three-dimensional ultrasonic image data, the second set of three-dimensional ultrasonic image data and/or the one-to-one registration mapping relationship, the image storage device coupled to the image collection unit and the image analysis unit.

3. The ultrasonic image analysis system of claim 1, wherein the first set of three-dimensional ultrasonic image data and the second set of three-dimensional ultrasonic image data obtained by the image collection unit are at least one of three-dimensional ultrasonic tissue image data and three-dimensional contrast enhanced ultrasonic image data.

4. The ultrasonic image analysis system of claim 1, wherein the image analysis unit comprises an automatic analysis sub-unit comprising the processor which automatically registers the second set of three-dimensional ultrasonic image data and the first set of three-dimensional ultrasonic image data to obtain the one-to-one registration mapping relationship.

5. The ultrasonic image analysis system of claim 4, wherein the processor automatically registers the second set of three-dimensional ultrasonic image data and the first set of three-dimensional ultrasonic image data based on similarity between the second set of three-dimensional ultrasonic image data and the first set of three-dimensional ultrasonic image data.

6. The ultrasonic image analysis system of claim 4, wherein the processor automatically registers the second set of three-dimensional ultrasonic image data and the first set of three-dimensional ultrasonic image data based on mapping between the second set of three-dimensional ultrasonic image data and the first set of three-dimensional ultrasonic image data.

7. The ultrasonic image analysis system of claim 1, wherein the image analysis unit comprises a semi-automatic analysis sub-unit comprising the processor which semi-automatically registers the second set of three-dimensional ultrasonic image data and the first set of three-dimensional ultrasonic image data in connection with a user interface device and the image display unit to obtain the one-to-one registration mapping relationship.

8. The ultrasonic image analysis system of claim 1, wherein the first set of three-dimensional ultrasonic image data is pre-operation image data, the second set of three-dimensional ultrasonic image data is post-operation image data.

9. An ultrasonic image analysis method for evaluating an ablative therapy, comprising:
prior to ablation of a tumor, transmitting ultrasonic waves using an ultrasonic probe to a target region containing a tumor and collecting a first set of three-dimensional ultrasonic image data corresponding to the target region; and
subsequent to ablation of the tumor;
displaying a pre-ablation section image from the first set of three-dimensional ultrasonic image data;
transmitting ultrasonic waves to the target region to obtain one or more post-ablation section images of the target region as a user changes a location of the ultrasonic probe;
when one of the one or more post-ablation section images is determined to be similar to the pre-ablation section image according to a similarity measurement function, transmitting ultrasonic waves to the target region at the location of the ultrasonic probe to obtain a second set of three-dimensional ultrasonic image data corresponding to the target region after ablation;
registering the second set of three-dimensional ultrasonic image data and the first set of three-dimensional ultrasonic image data to obtain a one-to-one registration mapping relationship between the first set of three-dimensional ultrasonic image data and the second set of three-dimensional ultrasonic image data, wherein the one-to-one registration mapping relationship is obtained from only either or both of the first set of three-dimensional ultrasonic image data and the second set of three-dimensional ultrasonic image data; and
comparatively displaying a pre-ablation image generated from the first set of three-dimensional ultrasonic image data in a first display area and a post-ablation image generated from the second set of three-dimensional ultrasonic image data based on the one-to-one registration mapping relationship in a second display area next to the first display area, and wherein the pre-ablation image and post-ablation image are displayed simultaneously;
wherein the first and second display areas are linked, such that a measuring operation performed on the tumor in the pre-ablation image is simultaneously displayed at a same position on the tumor in the post-ablation image, and measuring operation performed on the tumor in the post-ablation image is simultaneously displayed at a same position on the tumor in the pre-ablation image, in order to evaluate a therapeutic effect of the ablation, wherein the measuring operation comprises at least one of a distance measuring operation, an area measurement operation, or a tracing of the tumor.

10. The ultrasonic image analysis method of claim 9, further comprising:
storing the first set of three-dimensional ultrasonic image data, the second set of three-dimensional ultrasonic image data or the one-to-one registration mapping relationship.

11. The ultrasonic image analysis method of claim 9, wherein the first set of three-dimensional ultrasonic image data and the second set of three-dimensional ultrasonic image data are at least one of three-dimensional ultrasound tissue image data and three-dimensional contrast enhanced ultrasound image data.

12. The ultrasonic image analysis method of claim 9, wherein registering the first set of three-dimensional ultrasonic image data and the second set of three-dimensional ultrasonic image data comprises automatically registering the first set of three-dimensional ultrasonic image data and the second set of three-dimensional ultrasonic image data to obtain the one-to-one registration mapping relationship.

13. The ultrasonic image analysis method of claim 9, wherein registering the first set of three-dimensional ultrasonic image data and the second set of three-dimensional ultrasonic image data comprises semi-automatically registering the first set of three-dimensional ultrasonic image data and the second set of three-dimensional ultrasonic image data to obtain the one-to-one registration mapping relationship.

14. An ultrasonic image analysis method, comprising:
collecting, using an ultrasound probe prior to ablation of a tumor, a first set of three-dimensional ultrasonic image data corresponding to a target region containing the tumor; and
after ablation of the tumor:
displaying a pre-ablation section image from the first set of three-dimensional ultrasonic image data;
collecting one or more post-ablation section images of the target region as a user changes a location of the ultrasound probe;
when one of the one or more post-ablation section images is determined to be similar to the pre-ablation section image according to a similarity measurement function, collecting a second set of three-dimensional ultrasonic image data corresponding to the target region after ablation;
registering the first set of three-dimensional ultrasonic image data and the second set of three-dimensional ultrasonic image data to obtain a one-to-one registration mapping relationship between the first set of three-dimensional ultrasonic image data and the second set of three-dimensional ultrasonic image data through rigid registration using only content of either or both of the first set of three-dimensional ultrasonic image data and the second set of three-dimensional ultrasonic image data;
displaying a first image generated from the first set of three-dimensional ultrasonic image data in a first area of a display device; and
simultaneously and comparatively displaying a second image generated from the second set of three-dimensional ultrasonic image data based on the one-to-one registration mapping relationship in a second area of the display device next to the first area;
wherein the first and second areas are linked, such that a measuring operation performed on the tumor the first image is simultaneously displayed at a same position on the tumor in the second image, and measuring operation performed on the tumor in the second image is simultaneously displayed at a same position on the tumor in the first image, in order to evaluate a therapeutic effect of the ablation, wherein the measuring operation comprises at least one of a distance measuring operation, an area measurement operation, or a tracing of the tumor.

15. The ultrasonic image analysis method of claim 14, wherein each of the first image and the second image is one three-dimensional image or at least one section image of the target region.

16. An ultrasonic image analysis system for evaluating an ablative therapy, comprising:
an image collection unit comprising an ultrasonic probe and a processor, wherein, prior to ablation of a tumor, the image collection unit transmits ultrasonic waves to a target region containing the tumor and obtains a first set of three-dimensional ultrasonic image data corresponding to the target region before ablation; and
after ablation of the tumor, the image collection unit:
displays a pre-ablation section image from the first set of three-dimensional ultrasonic image data;
transmits ultrasonic waves to the target region and obtains one or more post-ablation section images of the target region as a user changes a location of the ultrasonic probe; and
when one of the one or more post-ablation section images is determined to be similar to the pre-ablation section image according to a similarity measurement function, transmits ultrasonic waves to the target region at the location of the ultrasonic probe and obtains a second set of three-dimensional ultrasonic image data corresponding to the target region after ablation;
an image analysis unit comprising the processor which registers the first set of three-dimensional ultrasonic image data and the second set of three-dimensional ultrasonic image data to obtain a one-to-one registration mapping relationship between the first set of three-dimensional ultrasonic image data and the second set of three-dimensional ultrasonic image data, wherein the one-to-one registration mapping relationship is obtained from only at least one of the first set of three-dimensional ultrasonic image data and the second set of three-dimensional ultrasonic image data, such that the first and second sets of three-dimensional ultrasonic image data have a same scale, translation, and rotation, the image analysis unit being coupled to the image collection unit; and
an image display unit comprising a screen region which comparatively displays a first image generated from the first set of three-dimensional ultrasonic image data and a second image generated from the second set of three-dimensional ultrasonic image data based on the one-to-one registration mapping relationship, the image display unit being coupled to the image analysis unit;
wherein the first image is displayed in a first sub-screen region of the screen region, and the second image is simultaneously displayed in a second sub-screen region of the screen region, the second sub-screen region being next to the first sub-screen region; and
wherein the first and second sub-screen regions are linked, such that a measuring operation performed on the tumor the first image is simultaneously displayed in a same position on the tumor in the second image, and measuring operation performed on the tumor in the second image is simultaneously displayed in the same position on the tumor in the first image, in order to evaluate a therapeutic effect of the ablation, wherein the measuring operation comprises at least one of a distance measuring operation, an area measurement operation, or a tracing of the tumor.

* * * * *